(12) United States Patent
Terrien et al.

(10) Patent No.: US 11,154,812 B2
(45) Date of Patent: *Oct. 26, 2021

(54) METHOD FOR PURIFYING A NATURAL GAS STREAM

(71) Applicants: L'Air Liquide, Société Anonyme pour l'Etude et l'Exploitation des Procédés Georges Claude, Paris (FR); Air Liquide Advanced Technologies U.S. LLC, Houston, TX (US)

(72) Inventors: Paul Terrien, Newton, MA (US); Pascal Marty, Bry sur marne (FR); Yong Ding, Waban, MA (US)

(73) Assignees: L'Air Liquide Societe Anonyme Pour L'Etude Et L'Exploitation Des Procedes Georges Claude, Paris (FR); Air Liquide Advanced Technologies U.S. LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/633,293

(22) PCT Filed: Jul. 23, 2018

(86) PCT No.: PCT/FR2018/051878
§ 371 (c)(1),
(2) Date: Jan. 23, 2020

(87) PCT Pub. No.: WO2019/020918
PCT Pub. Date: Jan. 31, 2019

(65) Prior Publication Data
US 2020/0139296 A1    May 7, 2020

(30) Foreign Application Priority Data
Jul. 27, 2017   (FR) ...................... 1757156

(51) Int. Cl.
*B01D 53/22*   (2006.01)
*C07C 7/144*   (2006.01)
(Continued)

(52) U.S. Cl.
CPC ......... *B01D 53/229* (2013.01); *B01D 53/002* (2013.01); *C07C 7/005* (2013.01);
(Continued)

(58) Field of Classification Search
None
See application file for complete search history.

(56) References Cited

U.S. PATENT DOCUMENTS 6,053,965 A    4/2000  Lokhandwala
6,361,582 B1   3/2002  Pinnau et al.
(Continued)

FOREIGN PATENT DOCUMENTS

CA    2 977 195    9/2016
CA    2 977 196    9/2016

OTHER PUBLICATIONS

Dortmundt, D. et al., Recent developments in $CO_2$ removal membrane technology, UOP LLC, Des Plaines, IL, 1999, 1-31.
(Continued)

*Primary Examiner* — Philip Y Louie
(74) *Attorney, Agent, or Firm* — Christopher J. Cronin

(57) ABSTRACT

A process for purifying a natural gas feed gas stream including methane and hydrocarbons, including step a): cooling the feed gas stream; step b): introducing the cooled stream into a first phase separator vessel in order to produce a liquid stream and a gas stream; step c): separating the gas stream resulting from step b) in a membrane unit from which a methane-enriched permeate stream and one partially condensed residue stream enriched in hydrocarbons exit; step d): introducing the residue stream resulting from step c) into
(Continued)

a second phase separator vessel to produce a liquid stream and a gas stream; step e): introducing at least one portion of the liquid stream resulting from step d) into a JT expansion means; step f): heating at least one portion of the expanded by introduction into the heat exchanger used in step a) counter-current to the feed stream.

8 Claims, 1 Drawing Sheet

(51) Int. Cl.
    *B01D 53/00*      (2006.01)
    *C07C 7/00*      (2006.01)
    *C07C 7/09*      (2006.01)
    *C10L 3/10*      (2006.01)

(52) U.S. Cl.
    CPC ................ *C07C 7/09* (2013.01); *C07C 7/144* (2013.01); *C10L 3/10* (2013.01); *C10L 2290/06* (2013.01); *C10L 2290/548* (2013.01); *F25J 2215/60* (2013.01)

(56) References Cited

U.S. PATENT DOCUMENTS

2006/0042463 A1    3/2006   Frantz
2014/0107388 A1    4/2014   Lokhandwala et al.

OTHER PUBLICATIONS

International Search Report and Written Opinion for corresponding PCT/FR2018/051878, dated Jan. 31, 2019.
International Search Report and Written Opinion for related PCT/FR2018/051877, dated Nov. 2, 2018.
International Search Report and Written Opinion for related PCT/FR2018/051876, dated Jan. 29, 2019.

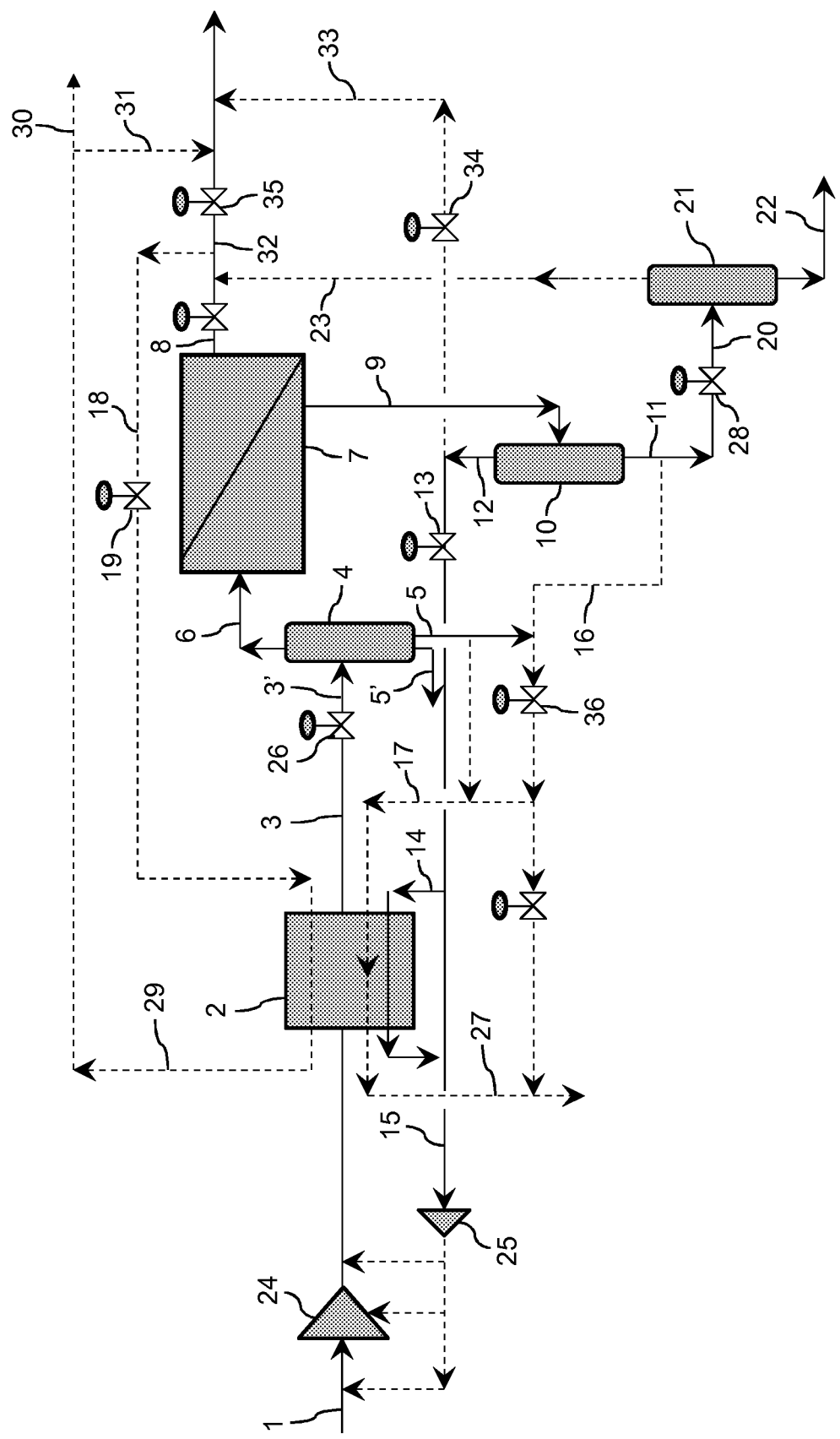

METHOD FOR PURIFYING A NATURAL GAS STREAM

CROSS REFERENCE TO RELATED APPLICATIONS

This application is a 371 of International PCT Application No. PCT/FR2018/051878, filed Jul. 23, 2018, which claims priority to French Patent Application No. 1757156, filed Jul. 27, 2017, the entire contents of which are incorporated herein by reference.

BACKGROUND

The present invention relates to a process for purifying a gas containing hydrocarbons heavier than methane, for example natural gas or a gas associated with oil production or a flare gas or a gaseous effluent from a refinery.

Most conventional units used for extracting natural gas liquids (NGLs) or liquid petroleum gases (LPGs) are cryogenic units. These are generally expensive and consume a lot of electricity. Some alternative membrane technologies make it possible to concentrate the natural gas liquids on the residue (retentate) side of a membrane. The Applicant has, for example, developed a polymer fiber, resistant to the formation of liquids and selective with respect to methane compared to hydrocarbons containing more than two or more than three carbon atoms: light hydrocarbons (and hydrogen) permeate while the partial pressure of heavier hydrocarbons increases on the high pressure side (residue side of the membrane) thus resulting in partial or even complete condensation of the heavy hydrocarbons.

SUMMARY

The inventors of the present invention have developed a solution enabling the separation of a gas stream into a methane-enriched fraction and a fraction enriched in C2 and higher hydrocarbons, minimizing the losses of methane during this removal and while minimizing the costs involved in the deployment of processes of this type.

The subject of the present invention is a process for purifying a natural gas feed gas stream comprising methane, and hydrocarbons containing at least two carbon atoms, comprising the following steps:
  Step a): cooling the feed gas stream in a heat exchanger;
  Step b): introducing the stream resulting from step a) into a first phase separator vessel in order to produce a liquid stream depleted in methane and enriched in hydrocarbons containing more than two carbon atoms and a gas stream;
  Step c): separating the gas stream resulting from step b) in a membrane permeation unit from which at least one methane-enriched gaseous permeate stream and one partially condensed residue stream enriched in hydrocarbons containing at least two carbon atoms exit;
  Step d): introducing the residue stream resulting from step c) into a second phase separator vessel in order to produce at least two phases including a liquid stream and a gas stream;
  Step e): introducing at least one portion of the liquid stream resulting from step d) into a Joule-Thomson expansion means;
  Step f): heating at least one portion of the expanded stream resulting from step e) by introduction into the heat exchanger used in step a) counter-current to the feed stream.

According to other embodiments, a subject of the invention is also:
  A process as defined above, characterized in that the heated stream resulting from step f) is recycled by mixing with the feed stream.
  A process as defined above, characterized in that at least one portion of the liquid stream resulting from step b) is mixed with said at least one portion of the liquid stream resulting from step d) before step e).
  A process as defined above, characterized in that at least one portion of the methane-enriched permeate stream resulting from step c) is heated by introduction into the heat exchanger used in step a) counter-current to the feed stream in order to cool the latter.
  A process as defined above, characterized in that said at least one portion of the permeate stream resulting from step d) undergoes a Joule-Thomson expansion prior to the introduction thereof into the heat exchanger.
  A process as defined above, characterized in that at least one portion of the liquid stream resulting from step d) is introduced into a third phase separator vessel in order to produce at least two phases, including a liquid stream and a gas stream.
  A process as defined above, characterized in that said gas stream at the outlet of the third phase separator vessel is heated by introduction into the heat exchanger used in step a) counter feed stream in order to cool the latter.
  A process as defined above, characterized in that said gas stream at the outlet of the third phase separator vessel is mixed with the permeate stream resulting from step c).

The expression "feed stream" as used in the present patent application relates to any composition containing hydrocarbons, including at least methane.

The heat exchanger may be any heat exchanger, any unit or other arrangement suitable for allowing the passage of a certain number of streams, and thus allowing direct or indirect exchange of heat between one or more refrigerant fluid lines and one or more feed streams.

Preferably, the purified stream (liquid fraction of the residue) comprises at least 50 mol % of hydrocarbons other than methane.

The membrane separation unit used during step c) has a greater selectivity for methane than for hydrocarbons containing at least two carbon atoms, preferably containing at least three carbon atoms and operates in the presence of liquid.

Methane or even hydrogen is found in the permeate stream at the outlet of the membrane unit while the hydrocarbons heavier than methane are on the residue (retentate) side, giving rise to a partial or complete condensation of the liquid residue stream rich in hydrocarbons comprising at least two carbon atoms.

The present invention consists of the combination of a membrane unit with partial or complete condensation on the residue (retentate) side and a heat exchanger between the feed gas cooled by the expanded gas fraction or the expanded liquid fraction of said residue in order to effectively separate methane from the heavier hydrocarbons. The lower temperature thus obtained for the feed stream makes it possible to increase the rate of formation of liquid hydrocarbons.

An example of use of the present invention is illustrated in the FIGURE by the following example.

BRIEF DESCRIPTION OF THE DRAWING

For a further understanding of the nature and objects for the present invention, reference should be made to the following detailed description, taken in conjunction with the accompanying drawings, in which like elements are given the same or analogous reference numbers and wherein:

The FIGURE illustrates one embodiment of the present invention.

DETAILED DESCRIPTION OF THE PREFERRED EMBODIMENTS

In the FIGURE, a natural gas feed stream 1 is introduced into a heat exchanger 2 at a temperature T1.

Typically the feed stream 1 may contain methane, ethane, propane, hydrocarbons containing at least four carbon atoms, $CO_2$, aromatics, nitrogen, water, sulfur compounds ($H_2S$ for example).

The feed stream 1 may be compressed via a compressor 24 for example, so that the pressure is sufficient for the correct implementation of the process according to the invention.

A partially condensed stream 3 leaves the heat exchanger 2 at a temperature T2 below T1.

The stream 3 is introduced into a phase separator vessel 4 from which a water-rich liquid stream 5', a liquid stream 5 rich in hydrocarbons containing at least two carbon atoms and a methane-enriched gas stream 6 emerge. The stream 3 may have been expanded to a stream 3', via a Joule Thomson valve 26 for example, before it enters the separator vessel 4.

The gas stream 6 is then introduced into a membrane separation unit 7 having a greater selectivity for methane than for hydrocarbons containing more than two carbon atoms and operating in the presence of formation of liquid on the residue (retentate) side. In this membrane unit 7, the stream is separated into a methane-enriched gaseous permeate stream 8, the pressure of which is lower than the pressure of the stream 6, and a partially condensed residue stream 9 enriched in at least one hydrocarbon containing more than two carbon atoms.

The stream 9 is introduced into a phase separator vessel 10. A liquid stream 11 rich in hydrocarbons containing at least two carbon atoms and a gas stream 12 emerge therefrom.

The gas stream 12 can then, at least in part, be heated 15 in the heat exchanger 2 to a temperature fairly close to T1 (i.e. to a temperature T4 strictly above T2 and at least between T2 and T1). The stream 12 is heated in the heat exchanger 2 in the counter direction to the feed stream 1 which, in itself, is cooled to the temperature T2.

The stream 15 can then optionally be mixed with the feed stream 1 in order to be recycled. This recycling may take place after passing through a dedicated compressor 25 depending on the requirements and operating conditions if a treated gas compressor 24 is not used.

Prior to entering the heat exchanger 2, the stream 12 is expanded 14 using a Joule-Thomson valve 13.

It is also possible to introduce the liquid streams 5 and 11, at least in part, independently or after having been mixed 17 and optionally expanded via a Joule Thomson valve 36, into the heat exchanger 2 in order to be heated 27 and partially (or even completely) vaporized and used to cool the feed stream 1.

A portion of the liquid stream 11 can be introduced into a phase separator vessel 21 after having been expanded 20 via a Joule Thomson valve 28. From this phase separator vessel 21, a liquid phase 22 enriched in heavy hydrocarbons and a gas phase 23 emerge.

The gas phase 23 and/or at least one portion 18 of the methane-enriched permeate stream 8 exiting the membrane unit 7 can be introduced (optionally after mixing), after an optional expansion 19, into the heat exchanger 2 in order to serve as a cold source for cooling the feed gas 1. This results in a stream 29 which will be able to serve, at least in part, as methane-enriched fuel 30 if need be. At least one other portion 31 of this stream 29 could be mixed again with the portion 32 of the permeate stream 8 which has not been sent to the heat exchanger 2.

It is also possible for a portion 33 of the gas stream 12 leaving the phase separator vessel 10 to be drawn off in order to be mixed with the stream 32 or with the stream 30.

This mixing may take place after expansions via Joule-Thomson valves 34 and 35 for example.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A process for purifying a natural gas feed gas stream comprising methane and hydrocarbons containing at least two carbon atoms, comprising the following steps:
    Step a): cooling the feed gas stream in a heat exchanger to produce a cooled feed gas stream;
    Step b): introducing the cooled feed gas stream resulting from step a) into a first phase separator vessel in order to produce a first liquid stream that is depleted in methane and enriched in hydrocarbons containing more than two carbon atoms and a first gas stream;
    Step c): separating the first gas stream resulting from step b) in a membrane permeation unit from which at least one methane-enriched gaseous permeate stream and one partially condensed residue stream enriched in hydrocarbons containing at least two carbon atoms exit;
    Step d): introducing the residue stream resulting from step c) into a second phase separator vessel in order to produce at least two phases including a second liquid stream and a second gas stream;
    Step e): introducing at least one portion of the second liquid stream resulting from step d) into a Joule-Thomson expansion means; and
    Step f): heating at least one portion of the expanded stream resulting from step e) by introduction into the heat exchanger used in step a) counter-current to the feed gas stream so as to produce at least one heated portion of the expanded stream resulting from step e).

2. The process as claimed in claim 1, wherein the at least one heated stream portion resulting from step f) is recycled by mixing with the feed gas stream.

3. The process as claimed in claim 1, wherein at least one portion of the first liquid stream resulting from step b) is mixed with said at least one portion of the second liquid stream resulting from step d) before step e).

4. The process as claimed in claim 1, wherein at least one portion of the at least one methane-enriched permeate stream resulting from step c) is heated by introduction into the heat exchanger used in step a) counter-current to the feed gas stream in order to cool the the feed gas stream.

5. The process as claimed in claim 4, wherein the at least one portion of the permeate stream resulting from step c) undergoes a Joule-Thomson expansion prior to the introduction thereof into the heat exchanger.

6. The process as claimed in claim 1, wherein at least one portion of the second liquid stream resulting from step d) is introduced into a third phase separator vessel in order to produce at least two phases, including a third liquid stream and a third gas stream.

7. The process as claimed in claim 6, wherein said third gas stream at an outlet of the third phase separator vessel is heated by introduction into the heat exchanger used in step a) counter-current to the feed gas stream in order to cool the the feed gas stream.

8. The process as claimed in claim 6, wherein the third gas stream at an outlet of the third phase separator vessel is mixed with the permeate stream resulting from step c).

* * * * *